(12) United States Patent
Ohtomo et al.

(10) Patent No.: US 11,305,999 B2
(45) Date of Patent: Apr. 19, 2022

(54) GRAPHENE NANORIBBON PRECURSOR AND METHOD FOR PRODUCING GRAPHENE NANORIBBON

(71) Applicant: FUJITSU LIMITED, Kawasaki (JP)

(72) Inventors: Manabu Ohtomo, Kawasaki (JP); Shintaro Sato, Atsugi (JP)

(73) Assignee: FUJITSU LIMITED, Kawasaki (JP)

( * ) Notice: Subject to any disclaimer, the term of this patent is extended or adjusted under 35 U.S.C. 154(b) by 134 days.

(21) Appl. No.: 16/812,424

(22) Filed: Mar. 9, 2020

(65) Prior Publication Data
US 2020/0308004 A1 Oct. 1, 2020

(30) Foreign Application Priority Data
Mar. 28, 2019 (JP) .............................. JP2019-063818

(51) Int. Cl.
*C01B 32/184* (2017.01)
(52) U.S. Cl.
CPC .................................. *C01B 32/184* (2017.08)
(58) Field of Classification Search
CPC ... C01B 32/184; C01B 2204/06; C01B 32/15; C01B 32/182; C01B 32/198; C01B 2204/00; C01B 2204/02; C01B 2204/04; C01B 2204/065; C01B 2204/20; C01B 2204/22; C01B 2204/24; C01B 2204/26; C01B 2204/28; C01B 2204/30; C01B 2204/32; C08G 2261/146; C08G 61/10; C07C 25/22
See application file for complete search history.

(56) References Cited

U.S. PATENT DOCUMENTS

| 2017/0062627 A1 | 3/2017 | Harada et al. |
| 2017/0081192 A1* | 3/2017 | Schwab ............. H01L 51/0045 |
| 2018/0362703 A1 | 12/2018 | Ohtomo |

FOREIGN PATENT DOCUMENTS

| JP | 2017-050424 A | 3/2017 |
| JP | 2017-057182 A | 3/2017 |

OTHER PUBLICATIONS

Chen, Zongping et al.,"Chemical Vapor Deposition Synthesis and Terahertz Photoconductivity of Low-Band-Gap N=9 Armchair Graphene Nanoribbons", Journal of the American Chemical Society, vol. 139, No. 10, Mar. 6, 2017, pp. 3635-3638, XP055722734.
Extended European Search Report dated Aug. 26, 2020 for corresponding European Patent Application No. 20162695.9.
Hironobu Hayashi et al., "Experimental and Theoretical Investigations of Surface-Assisted Graphene Nanoribbon Synthesis Featuring Carbon-Fluorine Bond Cleavage", ACS Nano, May 19, 2017, pp. 6204-6210 (Total 7 pages).

* cited by examiner

*Primary Examiner* — Daniel C. McCracken
(74) *Attorney, Agent, or Firm* — Fujitsu Patent Center

(57) ABSTRACT

A graphene nanoribbon precursor having a structural formula represented by a following chemical formula (1), wherein in the following chemical formula (1): n is an integer greater than or equal to 0; X is bromine, iodine or chlorine; and Y is hydrogen or fluorine.

5 Claims, 13 Drawing Sheets

GRAPHENE NANORIBBON PRECURSOR AND METHOD FOR PRODUCING GRAPHENE NANORIBBON

CROSS-REFERENCE TO RELATED APPLICATION

This application is based upon and claims the benefit of priority of the prior Japanese Patent Application No. 2019-63818, filed on Mar. 28, 2019, the entire contents of which are incorporated herein by reference.

FIELD

The embodiments discussed herein are related to a graphene nanoribbon precursor and a method for producing a graphene nanoribbon.

BACKGROUND

As nano-sized graphene, a quasi-one-dimensional graphene of a ribbon shape with a width of several nanometers, which is called a graphene nanoribbon (GNR) is known. It is known that the GNR has a band gap whose size is roughly inversely proportional to the width.

As an application of the GNR, there is a semiconductor device having a PN junction. The GNR tends to operate as a P-type semiconductor due to doping derived from oxygen in the atmosphere. On the other hand, it is difficult to produce a GNR that operates as an N-type semiconductor. Theoretically, it is considered possible to make a GNR operate as an N-type semiconductor by replacing hydrogen (H) at an edge of a GNR whose edge structure is of armchair type with fluorine (F). However, it has been impossible to stably produce a GNR whose edge structure is of armchair type and whose edge hydrogen is replaced with fluorine. In view of the above, it is desirable to be able to provide a graphene nanoribbon precursor that is capable of stably producing a graphene nanoribbon whose edge structure is of armchair type and whose edge hydrogen is replaced with fluorine, and a method for producing the graphene nanoribbon.

Japanese Laid-open Patent Publication No. 2017-57182, Japanese Laid-open Patent Publication No. 2017-50424 and *ACS Nano* 11, 6204 (2017) are disclosed as related art.

SUMMARY

According to an aspect of the embodiments, a graphene nanoribbon precursor having a structural formula represented by a following chemical formula (1), wherein in the following chemical formula (1): n is an integer greater than or equal to 0; X is bromine, iodine or chlorine; and Y is hydrogen or fluorine.

[Chemical Formula 1]

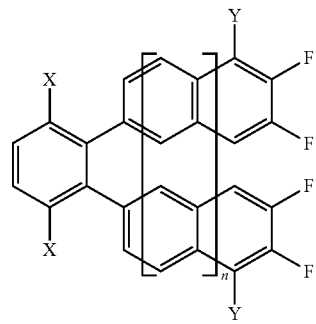

(1)

The object and advantages of the invention will be realized and attained by means of the elements and combinations particularly pointed out in the claims.

It is to be understood that both the foregoing general description and the following detailed description are exemplary and explanatory and are not restrictive of the invention.

DESCRIPTION OF EMBODIMENTS

Figure 1:
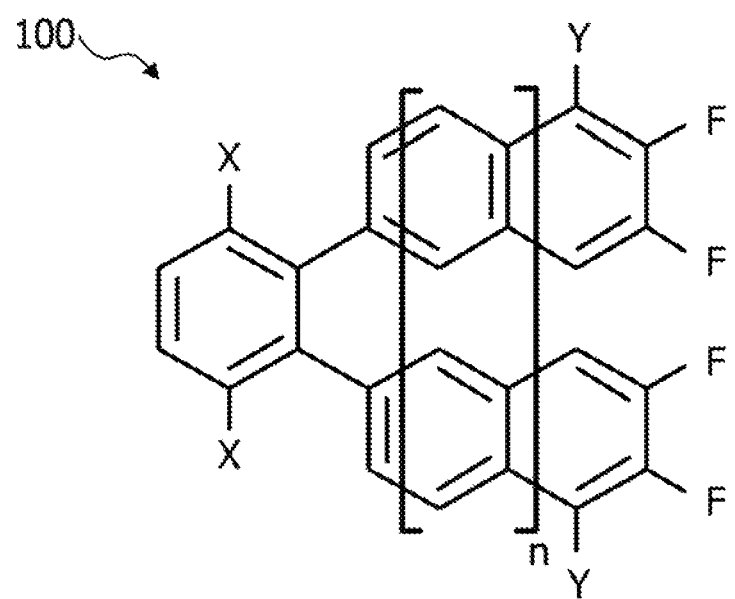
FIG. 1 is a diagram illustrating a structural formula of a GNR precursor according to a first embodiment.

Embodiments of the present disclosure will be specifically described below with reference to the accompanying drawings. Note that, in this specification and the drawings, components having substantially the same functional configuration are denoted by the same reference numerals, and explanation thereof will not be unnecessarily repeated.

First Embodiment

A first embodiment relates to a graphene nanoribbon (GNR) precursor that is suitable for producing a GNR. FIG. 1 is a diagram illustrating a structural formula of the GNR precursor according to the first embodiment.

A GNR precursor 100 according to the first embodiment has the structural formula illustrated in FIG. 1. In FIG. 1, n is an integer greater than or equal to 0, X is bromine (Br), iodine (I) or chlorine (CI), and Y is hydrogen (H) or fluorine (F).

Figure 2A:
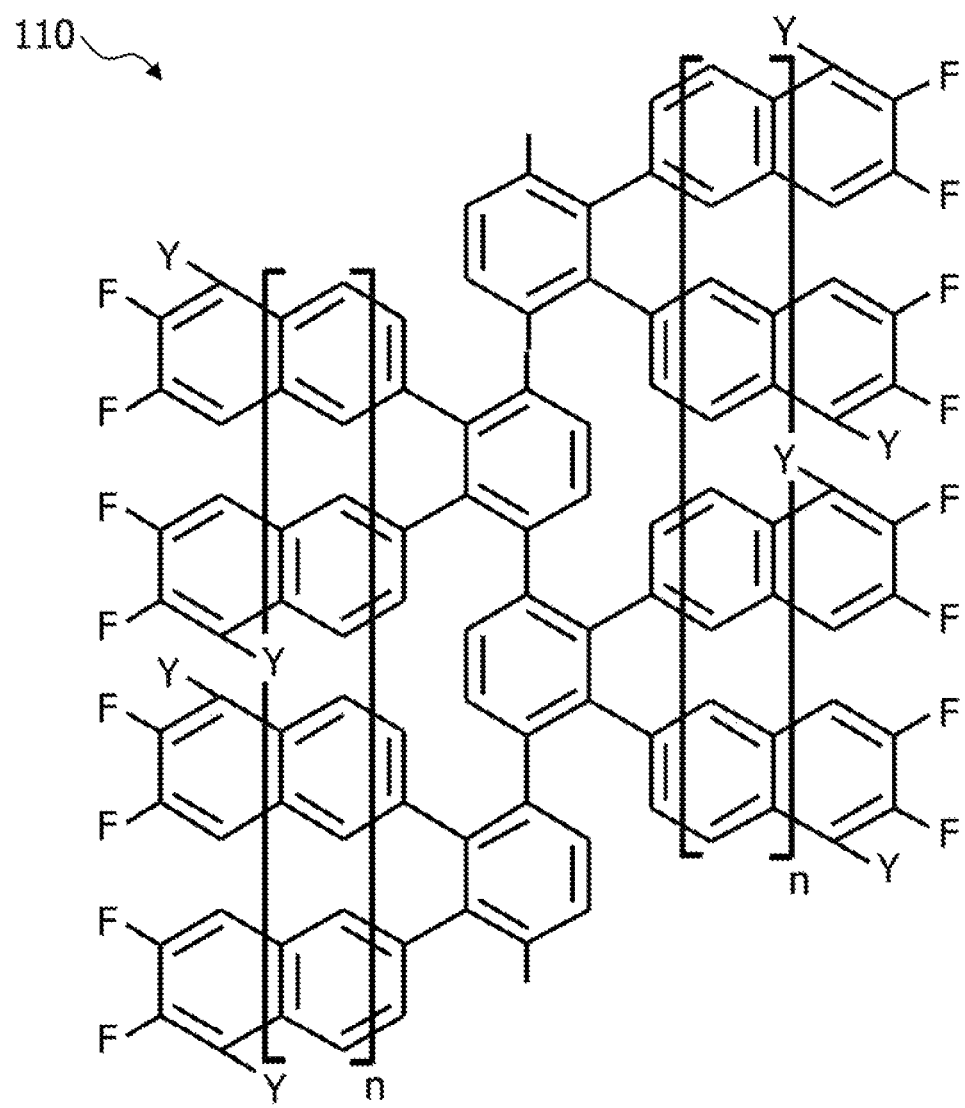
FIG. 2A is a diagram (part 1) illustrating a method for producing a GNR using the GNR precursors according to the first embodiment.
Figure 2B:
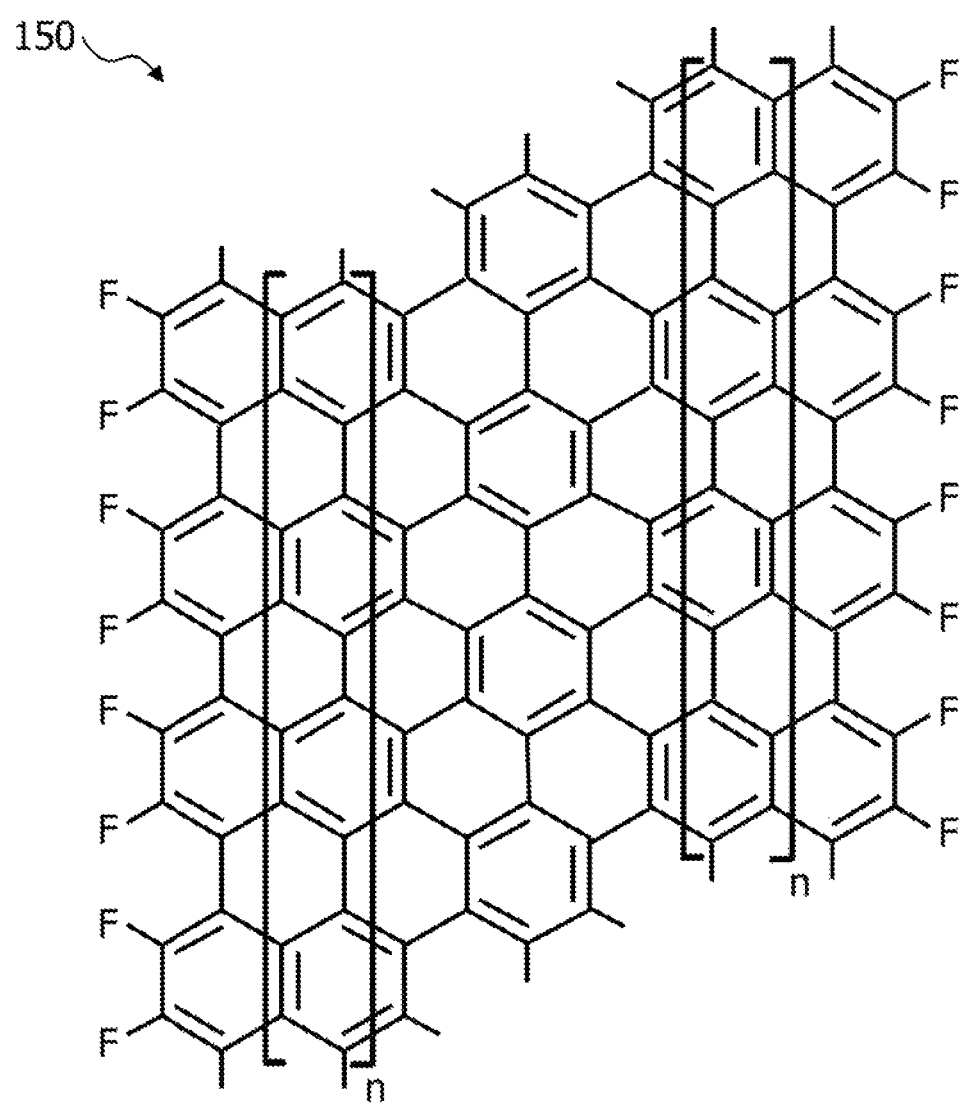
FIG. 2B is a diagram (part 2) illustrating the method for producing the GNR using the GNR precursors according to the first embodiment.

Here, a method for producing the GNR using the GNR precursors 100 according to the first embodiment will be described. FIGS. 2A and 2B are diagrams illustrating a method for producing the GNR using the GNR precursors according to the first embodiment.

First, a surface cleaning process of a catalytic metal substrate on which the GNR is grown is performed in an ultrahigh vacuum. By the surface cleaning process, organic contaminants on the surface of the catalytic metal substrate may be removed and the surface flatness may be enhanced. As the catalytic metal substrate, for example, a gold (Au) substrate, a silver (Ag) substrate or a copper (Cu) substrate having a Miller index on the surface of (111), (110), (100) or (788) may be used.

Next, without exposing the catalytic metal substrate subjected to the surface cleaning process to the atmosphere, the catalytic metal substrate is heated such that the surface temperature of the catalytic metal substrate is a first temperature which is equal to or higher than the elimination temperature $T_X$ of X and lower than the elimination temperature $T_Y$ of Y atoms, for example, 200° C. to 300° C., under an ultra-high vacuum, and the surface temperature of the catalytic metal substrate is held at the first temperature. Then, the GNR precursors 100 are vacuum-deposited on the surface of the catalytic metal substrate. It is desirable to control a deposition amount of the GNR precursor 100 so that about one-molecule layer will be formed. On the surface of the catalytic metal substrate'whose temperature is the first temperature, X atoms are eliminated from the GNR precursors 100 to cause an Ullmann reaction, and a C—C binding reaction is induced. As a result, as illustrated in FIG. 2A, a polymer 110 in which aromatic compounds are connected and in which a plurality of molecules of the GNR precursors 100 are arranged in one direction while reversing the direction of protrusion, is stably formed.

Next, the catalytic metal substrate is heated such that the surface temperature thereof is a second temperature, which is equal to or higher than the elimination temperature $T_H$ of H, for example, 350° C. to 450° C., and the surface temperature of the catalytic metal substrate is held at the second temperature. As a result, as illustrated in FIG. 2B, H and Y are eliminated from the polymer 110 and a C—C binding reaction is induced to aromatize the polymer 110, and a GNR 150 whose edge structure is of armchair type and whose edge H is replaced with F is formed.

In this way, upon heating the GNR precursors 100, X's are eliminated and C's, to which X's have been bound, are bound with each other between the GNR precursors 100, and thereafter, H's and Y's are eliminated and, then C's, to which H's have been bound, are bound with each other between the GNR precursors 100 and C's, to which Y's have been bound, are bound with each other between the GNR precursors 100. The sequence of the GNR precursors 100 is determined by bonding of C's, to which X's have been bound, with each other, and then the structure of the GNR 150 is fixed by subsequent bonding of C's, to which H's have been bound, with each other and bonding of C's, to which Y's have been bound, with each other, Therefore, it is possible to stably produce the GNR 150 whose edge structure is of armchair type and whose edge H is replaced with F.

Figure 3A:
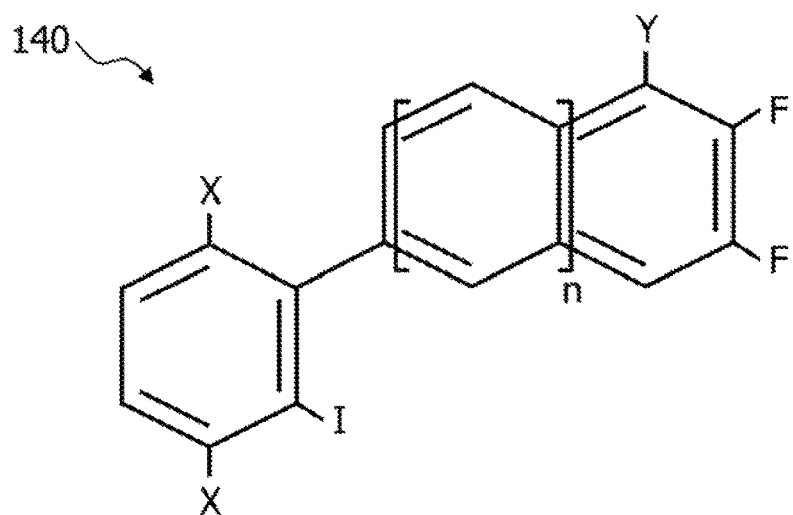
FIG. 3A is a diagram (part 1) illustrating a method for producing the GNR precursor according to the first embodiment.
Figure 3B:
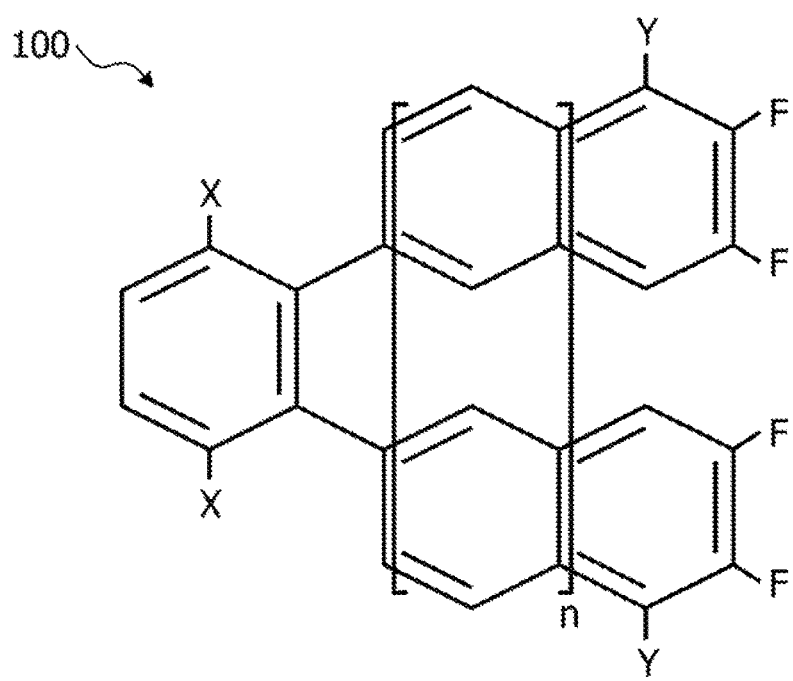
FIG. 3B is a diagram (part 2) illustrating the r meth for producing the GNR precursor according to the first embodiment.

Next, a method for producing the GNR precursor 100 according to the first embodiment will be described. FIGS. 3A and 3B are diagrams illustrating the method for producing the GNR precursor 100 according to the first embodiment.

Figure 4A:
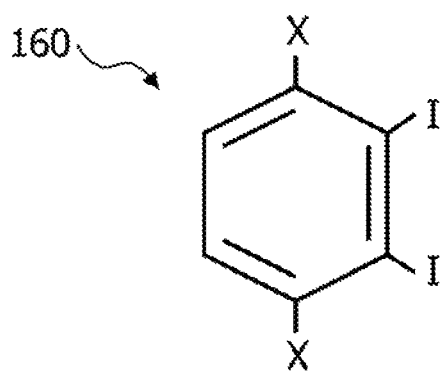
FIG. 4A is a diagram (part 1) illustrating a structural form a material of the GNR precursor according to the first embodiment.
Figure 4B:
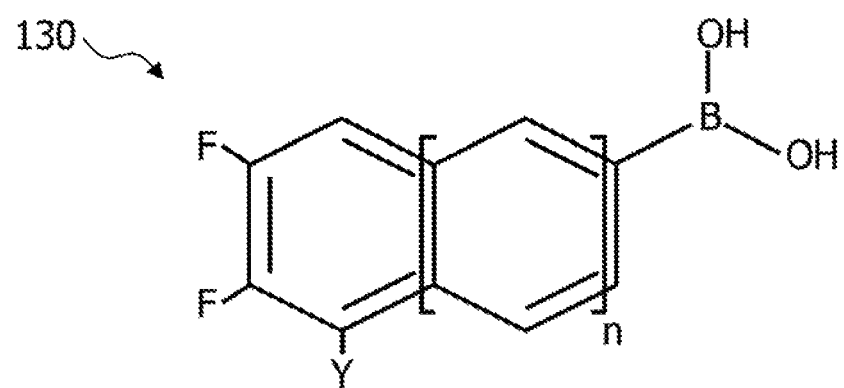
FIG. 4B is a diagram (part 2) illustrating a structural formula of a material of the GNR precursor according to the first embodiment.

First, a substance 160 whose structural formula is illustrated in FIG. 4A and a substance 130 whose structural formula is illustrated in FIG. 4B are prepared. The substance 160 illustrated in FIG. 4A is 1,4-dibromo-2,3-diiodobenzene, and the substance 130 illustrated in FIG. 4B is a boronic acid of benzene or an acene. As the acene, for example, naphthalene, anthracene, naphthacene, pentacene or hexacene may be used.

Next, these substances are dissolved in a solvent, a catalyst is added thereto and the mixture is stirred in the presence of a base to cause a Suzuki coupling reaction. By continuing stirring to evaporate the solvent, as illustrated in FIG. 3A, a substance 140 obtainable by monocoupling of one iodine (I) contained in the substance 160 with the substance 130 may be obtained.

Thereafter, the substance 140 illustrated in FIG. 3A and the substance 130 are dissolved in a solvent, a catalyst is added thereto and the mixture is stirred in the presence of a base to cause a Suzuki coupling reaction. By continuing stirring to evaporate the solvent, as illustrated in FIG. 3B, the GNR precursor 100 obtainable by monocoupling of iodine (I) contained in the substance 140 with the substance 130 may be obtained.

Then purification of the GNR precursor 100 is carried out, for example, by column chromatography.

In this way, the GNR precursor 100 may be produced by a bottom-up method.

Figure 5:
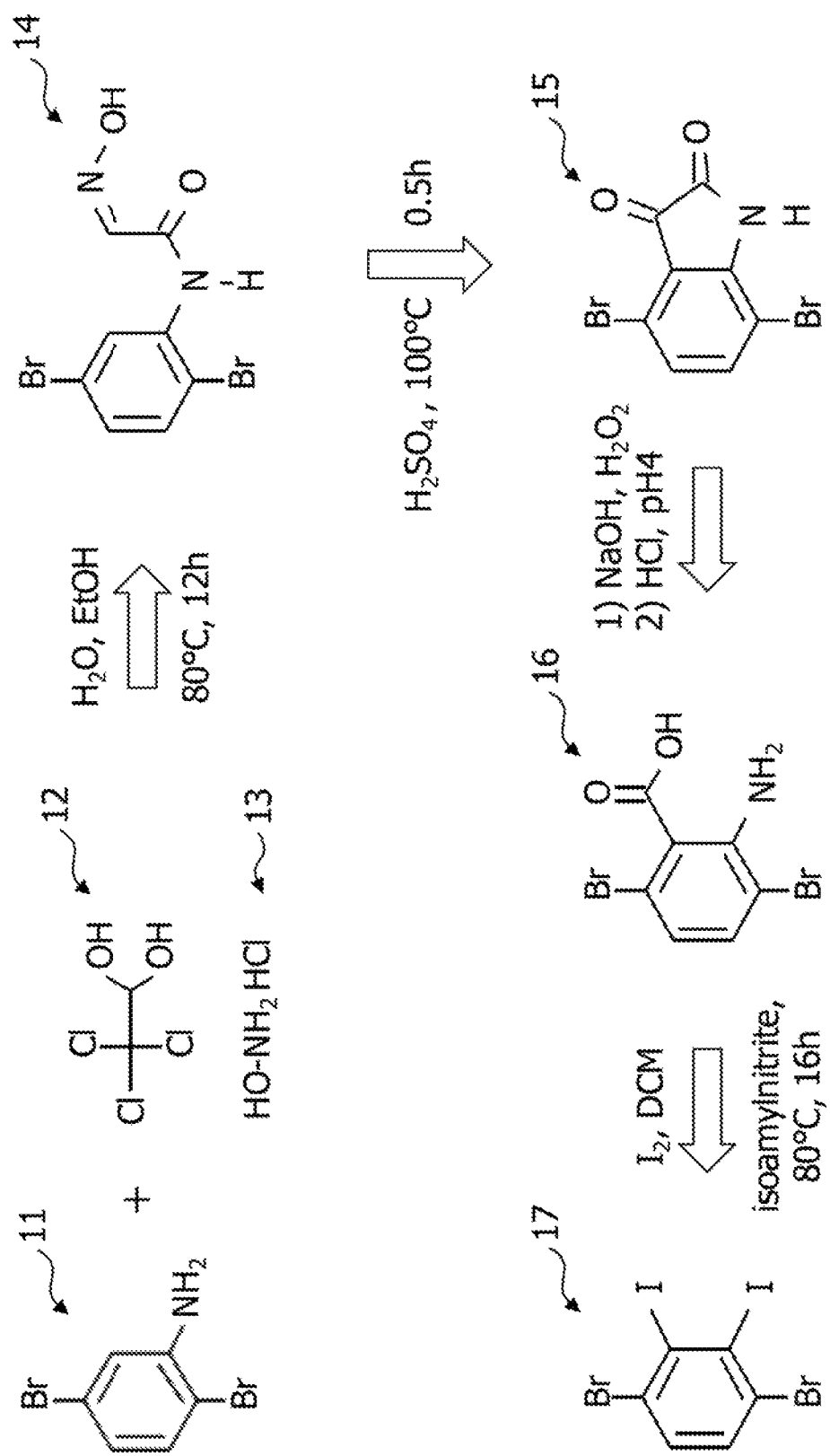
FIG. 5 is a diagram illustrating a method for synthesizing 1,4-dibromo-2,3-diiodobenzene.

1,4-dibromo-2,3-diiodobenzene may be synthesized, for example, by the following method. FIG. 5 is a diagram illustrating a method for synthesizing 1,4-dibromo-2,3-diiodobenzene.

First, 2,5-dibromoaniline (compound 11), chloral hydrate (compound 12) and hydroxylammonium chloride (compound 13) are reacted in an aqueous solution of ethanol to give (2,5-dibromophenyl)-2-(hydroxyimino)acetamide (compound 14). This reaction is carried out, for example, at 80° C. for 12 hours.

Next, (2,5-dibromophenyl)-2-(hydroxyimino)acetamide (compound 14) is added to concentrated sulfuric acid and the mixture is heated to give 4,7-dibromoindoline-2,3-dione (compound 15). This reaction is carried out, for example, at 100° C. for 30 minutes.

Thereafter, 4,7-dibromoindoline-2,3-dione (compound 15) is dissolved in a sodium hydroxide aqueous solution, a hydrogen peroxide solution is added dropwise thereto and the mixture is stirred. Subsequently, filtration is performed, hydrogen is added to the carboxyl group using hydrochloric acid, and the pH is adjusted to 4. Then, filtration is carried out to give 2-amino-3,6-dibromobenzoic acid (compound 16).

Next, 2-amino-3,6-dibromobenzoic acid (compound 16) is added dropwise to a solution of 1,2-dichloromethane, iodine and isoamyl nitrite to give 1,4-dibromo-2,3-diiodobenzene (compound 17). This reaction is carried out, for example, at 80° C. for 16 hours.

In this way, 1,4-dibromo-2,3-diiodobenzene may be synthesized.

Note that n is not particularly limited as long as it is an integer greater than or equal to 0, but in order to obtain a stable GNR precursor 100, n is preferably an integer greater than or equal to 0 and less than or equal to 5. Furthermore, the length of a GNR is not particularly limited, and may be, for example, several tens of nanometers. When iodine is used as X, it is easy to produce a long GNR.

Second Embodiment

Figure 6:
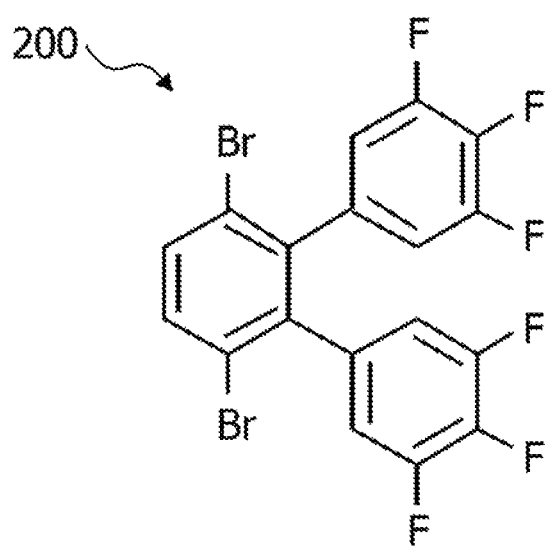
FIG. 6 is a diagram illustrating a structural formula of a GNR precursor according to a second embodiment.

A second embodiment relates to a GNR precursor that is suitable for producing a GNR. FIG. 6 is a diagram illustrating a structural formula of the GNR precursor according to the second embodiment.

A GNR precursor 200 according to the second embodiment has the structural formula illustrated in FIG. 6. That is, the GNR precursor 200 according to the second embodiment has the structural formula illustrated in FIG. 1 where n is 0, X is Br, and Y is F. The GNR precursor 200 is, so to speak, 3',6'-dibromo-3',3'',4',4'',5',5''-hexafluoro-1,1':2',1''-terphenyl.

Figure 7A:
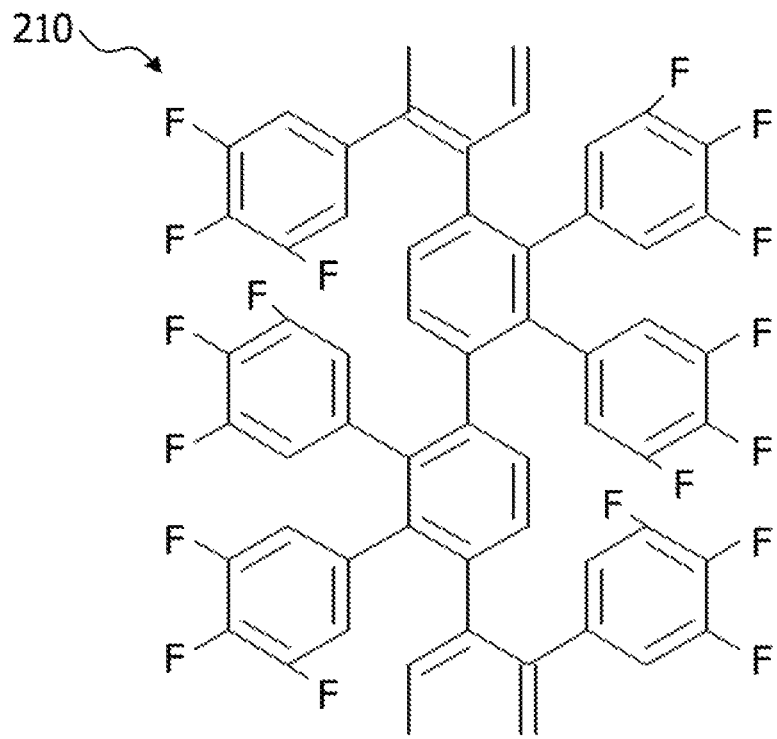
FIG. 7A is a diagram (part 1) illustrating a method for producing a GNR using the GNR precursors according to the second embodiment.
Figure 7B:
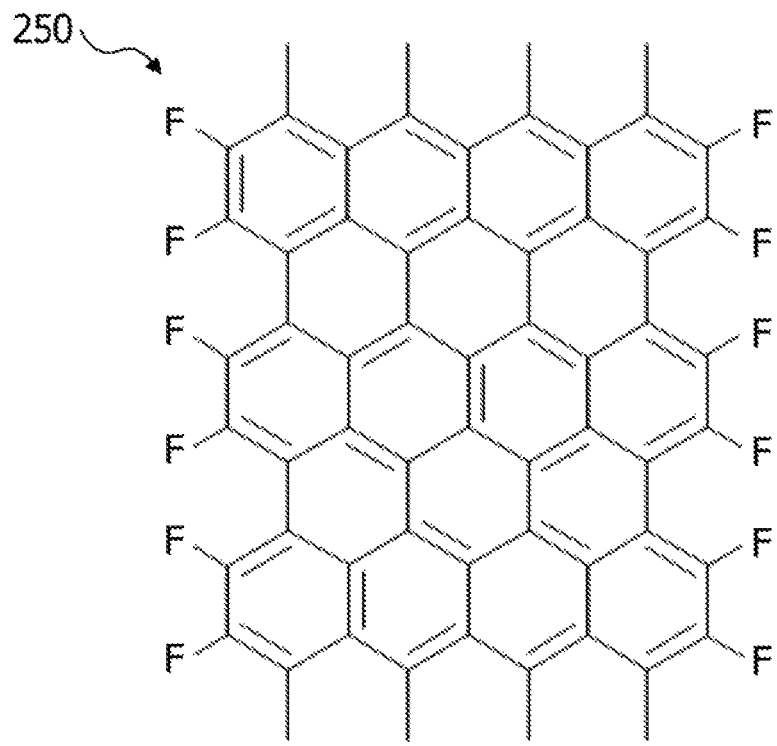
FIG. 7B is a diagram (part 2) illustrating the method for producing the GNR using the GNR precursors according to the second embodiment.

Here, a method for producing the GNR using the GNR precursors 200 according to the second embodiment will be described FIGS. 7A and 7B are diagrams illustrating a method for producing the GNR using the GNR precursors according to the second embodiment.

First, a surface cleaning process of a catalytic metal substrate on which the GNR is grown is performed in an ultrahigh vacuum. In this surface cleaning process, for example, Ar ion sputtering to the surface and annealing under an ultra-high vacuum are set as one cycle, and this cycle is performed for a plurality of cycles. For example, in each cycle, in the Ar ion sputtering, the ion acceleration voltage is set to 1.0 kV, the ion current is set to 10 µA, and the time is set to 1 minute, and in the annealing, while maintaining the degree of vacuum of $5 \times 10^{-7}$ Pa or less, the temperature is set to 400° C. to 500° C. and the time is set to 10 minutes. For example, the number of cycles is three (three cycles). By the surface cleaning process, organic contaminants on the surface of the catalytic metal substrate may be removed and the surface flatness may be enhanced. Here, a gold (Au) substrate having a Miller index on the surface of (111) is used as the catalytic metal substrate. Hereinafter, the (111) plane of the Au substrate is sometimes referred to as an "Au (111) plane".

Next, without exposing the catalytic metal substrate subjected to the surface cleaning process to the atmosphere, the catalytic metal substrate is heated such that the surface temperature of the catalytic metal substrate is a first temperature which is equal to or higher than the elimination temperature of Br and lower than the elimination temperature of H, for example, 200° C., under an ultra-high vacuum, and the surface temperature of the catalytic metal substrate is held at the first temperature. Then, the GNR precursors 200 are vacuum-deposited on the surface of the catalytic metal substrate. It is desirable to control a deposition amount of the GNR precursors 200 so that about one-molecule layer will be formed. On the surface of the catalytic metal substrate whose temperature is the first temperature, Br is eliminated from the GNR precursors 200 to cause an Ullmann reaction, and a C—C binding reaction is induced. As a result, as illustrated in FIG. 7A, a polymer 210 in which aromatic compounds are connected and in which a plurality of molecules of the GNR precursors 200 are arranged in one direction while reversing the direction of protrusion, is stably formed.

Next, the catalytic metal substrate is heated such that the surface temperature thereof is a second temperature, which is equal to or higher than the elimination temperature $T_H$ of H, for example, 400° C., and the surface temperature of the catalytic metal substrate is held at the second temperature. As a result, as illustrated in FIG. 7B, H and F are eliminated from the polymer 210 and a C—C binding reaction is induced to aromatize the polymer 210, and a GNR 250 whose edge structure is of armchair type and whose edge H is replaced with F is formed.

In this way, upon heating the GNR precursors 200, Br's are eliminated and C's, to which Br's have been bound, are bound with each other between the GNR precursors 200, and thereafter, H's and F's are eliminated and then C's, to which H's have been bound, are bound with each other between the GNR precursors 200 and C's, to which F's have been bound, are bound with each other between the GNR precursors 200. The sequence of the GNR precursors 200 is determined by bonding of C's, to which Br's have been bound, with each other, and then the structure of the GNR 250 is fixed by subsequent bonding of C's, to which H's have been bound, with each other and bonding of C's, to which F's have been bound, with each other, Therefore, it is possible to stably produce the GNR 250 whose edge structure is of armchair type and whose edge H is replaced with F.

Next, a method for producing the GNR precursor 200 according to the second embodiment will be described.

First, 1,4-dibromo-2,3-diiodobenzene and 3,4,5-trifluorophenylboronic acid are prepared, 3,4,5-Trifluorophenylboronic acid has a structural formula illustrated in FIG. 4B in which n is 0.

Next, by a method similar to that of the method for producing the GNR precursor 100 according to the first embodiment, Suzuki coupling reactions are caused twice and the solvent is evaporated to give the GNR precursor 200. Then, purification of the GNR precursor 200 is carried out, for example, by column chromatography.

In this way, the GNR precursor 200 may be produced by a bottom-up method.

Figure 8A:
FIG. 8A is a diagram illustrating a scanning tunneling microscope (STM) image of the GNR according to the second embodiment.
Figure 8B:
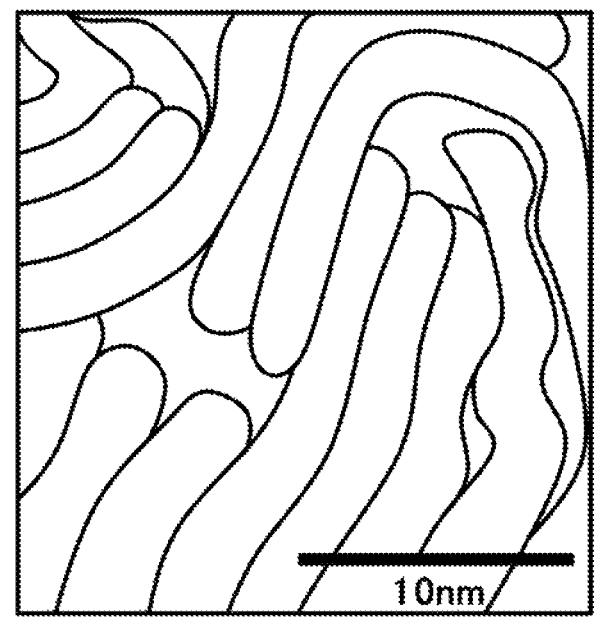
FIG. 8B is a diagram schematically illustrating the contents of the STM photograph illustrated in FIG. 8A.

FIG. 8A illustrates a scanning tunneling microscope (STM) image of the GNR produced according to the second embodiment. FIG. 8B is a diagram schematically illustrating the contents of the STM photograph illustrated in FIG. 8A.

As illustrated in FIGS. 8A and 8B, a one-dimensional structure having a width of slightly less than 1.5 nm, a length of about 10 nm to about 20 nm, and a thickness of about a monoatomic layer was obtained. That is, it was confirmed that a GNR was produced.

Figure 9A:
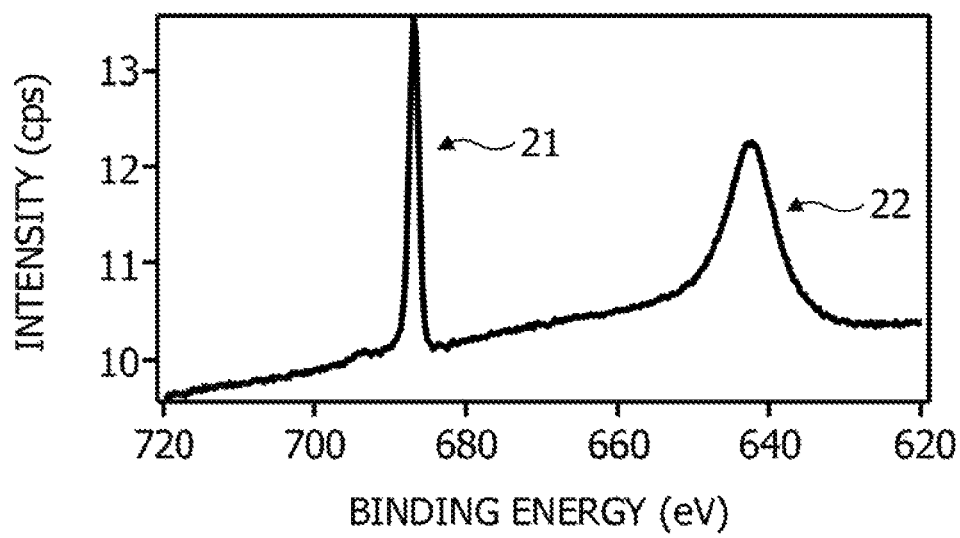
FIG. 9A is a diagram (part 1) illustrating an X-ray photoelectron spectroscopy spectrum.
Figure 9B:
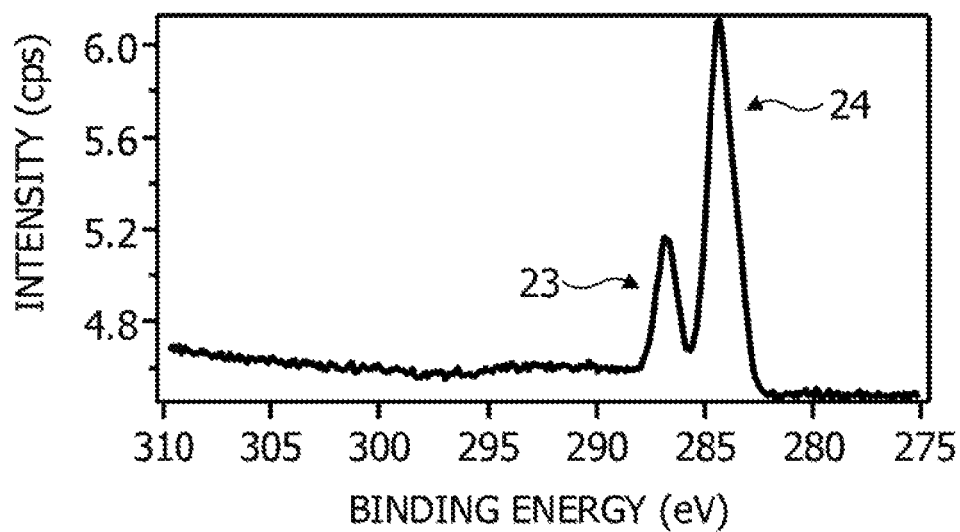
FIG. 9B is a diagram (part 2) illustrating an X-ray photoelectron spectroscopy spectrum.
Figure 9C:
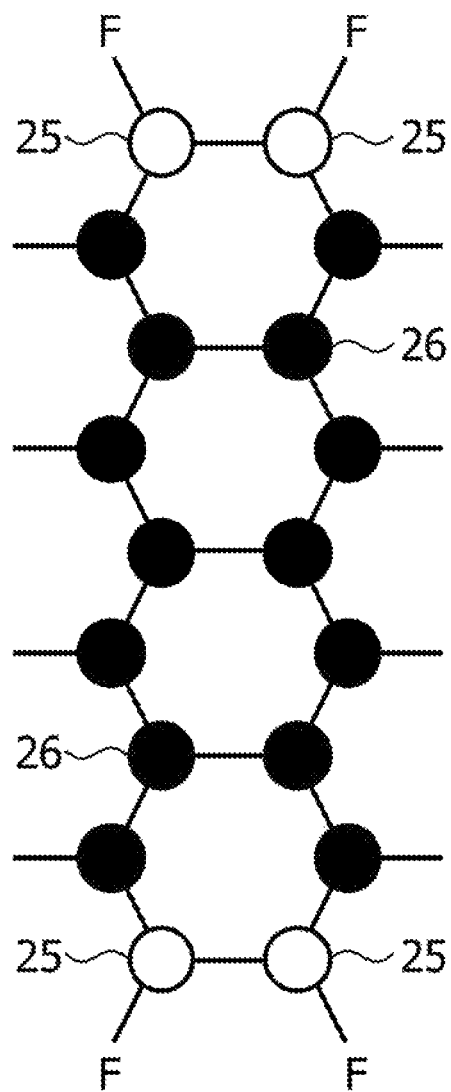
FIG. 9C is a schematic diagram illustrating the arrangement of C atoms between a pair of armchairs.

FIGS. 9A and 9B illustrate X-ray photoelectron spectroscopy (XPS) spectra of the produced GNR. As illustrated in FIG. 9A, a peak 21 of the 1s orbit of fluorine was confirmed in addition to a peak 22 of the 4p orbit of Au of the catalytic metal substrate. Furthermore, as illustrated in FIG. 9B, a peak 23 of C-F bond and a peak 24 of C of the 1s orbit located inside edges were confirmed. The intensity of the peak 24 is 3.4 times the intensity of the peak 23. As illustrated in FIG. 9C, when focusing on a pair of armchairs, the number of C atoms 26 located inside edges is 14, and the number of C atoms 25 located at the edges and bound to F atoms is 4. Therefore, the number of the C atoms 26 is 3.5 times the number of the C atoms 25. From this, it may be said that F atoms are bound to almost all the C atoms 25 located at the edges.

Figure 10:
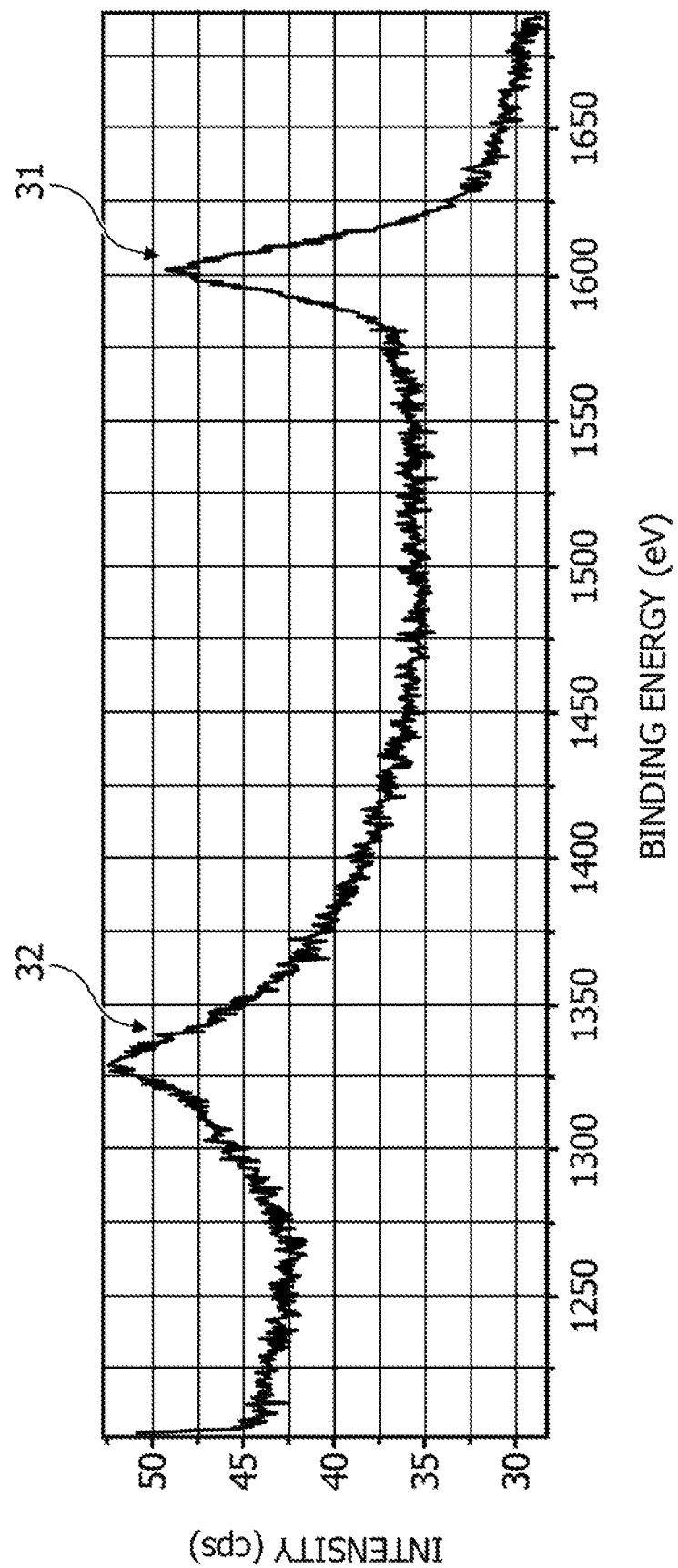
FIG. 10 is a diagram illustrating a microscopic Raman optical spectrum.

FIG. 10 illustrates a microscopic Raman optical spectrum of the produced GNR. As illustrated in FIG. 10, a peak 31 of the G band indicating the presence of graphene was confirmed. Furthermore, a peak 32 of the D band indicating that the GNR was of armchair type was also confirmed.

From the results illustrated in FIGS. 9A, 9B and 10, it was confirmed that a GNR whose edge structure is of armchair type and whose edge H is replaced with F was produced.

Figure 11:
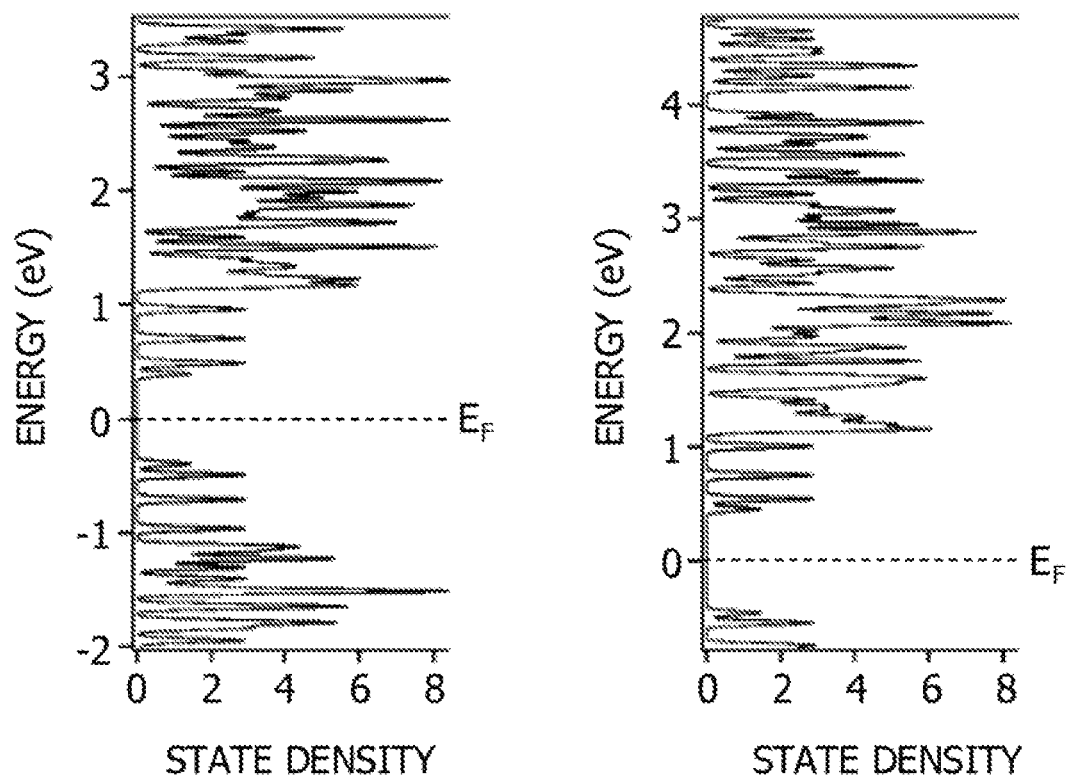
FIG. 11 is a diagram illustrating the electronic structures of 9AGNR and F-9AGNR side by side.

FIG. 11 illustrates electronic structures of 9AGNR and F-9AGNR side by side. 9AGNR is a GNR of armchair type in which four six-membered rings are arranged in the ribbon width direction and which has a width of nine carbon atoms. F-9AGNR is obtainable from 9AGNR by replacing the edge H of 9AGNR with F. When the electronic states of 9AGNR and F-9AGNR were calculated by density functional theory (DFT), the work function of F-9AGNR was 4.75 eV, and the work function of 9AGNR was 3.50 eV. This indicates that a PN junction may be realized by joining 9AGNR and F-9AGNR.

All examples and conditional language provided herein are intended for the pedagogical purposes of aiding the reader in understanding the invention and the concepts contributed by the inventor to further the art, and are not to be construed as limitations to such specifically recited examples and conditions nor does the or of such examples in the specification relate to a showing of the superiority and inferiority of the invention. Although one or more embodiments of the present invention have been described in detail, it should be understood that the various changes, substitutions, and alterations could be made hereto without departing from the spirit and scope of the invention.

What is claimed is:

1. A graphene nanoribbon precursor having a structural formula represented by a following chemical formula (1), wherein the following chemical formula (1) has a first case where n is 0; X is bromine, iodine or chlorine; and Y is fluorine and a second case where n is an integer greater than or equal to 1; X is bromine, iodine or chlorine; and Y is hydrogen or fluorine.

[Chemical Formula 1]

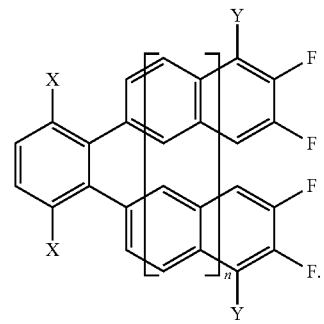

(1)

2. The graphene nanoribbon precursor according to claim 1, wherein n is an integer greater than or equal to 0 and less than or equal to 5.

3. A method of producing a graphene nanoribbon, the method comprising:
heating a graphene nanoribbon precursor to a first temperature on a substrate to induce elimination of X and a C—C binding reaction to obtain a polymer on the substrate; and
heating the polymer to a second temperature that is higher than the first temperature to induce elimination of H and Y and a C—C binding reaction,
the graphene nanoribbon precursor having a structural formula represented by a following chemical formula (1), wherein in the following chemical formula (1) has a first case where n is 0; X is bromine, iodine or chlorine; and Y is fluorine and a second case where n is an integer greater than or equal to 1; X is bromine, iodine or chlorine; and Y is hydrogen or fluorine.

[Chemical Formula 1]

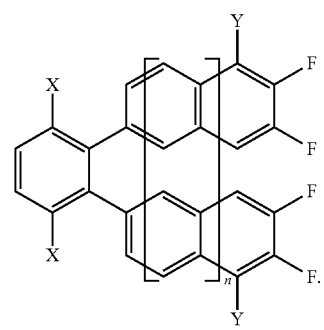

(1)

4. The method according to claim 3, wherein the C—C binding reaction is induced by an Ullmann reaction caused by eliminating the X atoms from the graphene nanoribbon precursors.

5. The method according to claim 3, wherein the polymer is a polymer in which aromatic compounds are connected and in which a plurality of molecules of the graphene nanoribbon precursors are arranged in one direction while reversing the direction of protrusion.

* * * * *